United States Patent [19]

Arakawa et al.

[11] Patent Number: 4,665,237

[45] Date of Patent: May 12, 1987

[54] PROCESS FOR PRODUCING METHYL TERTIARY BUTYL ETHER

[75] Inventors: Shinichi Arakawa; Masashi Araki; Masaaki Okamura, all of Chiba, Japan

[73] Assignee: Sumitomo Chemical Company, Limited, Osaka, Japan

[21] Appl. No.: 871,215

[22] Filed: Jun. 5, 1986

[30] Foreign Application Priority Data

Jun. 5, 1985 [JP] Japan .................................. 60-121943

[51] Int. Cl.$^4$ ........................ C07C 41/06; C07C 41/38
[52] U.S. Cl. ...................................... 568/697; 568/699
[58] Field of Search ................................ 568/697, 699

[56] References Cited

U.S. PATENT DOCUMENTS 4,219,678  8/1980  Obenaus et al. .

OTHER PUBLICATIONS

Scheeline et al, "Methyl Tertiary-butyl Ether", SRI International, Process Economic Reviews, Report No. 78-1-3, Dec. 1978.

*Primary Examiner*—Howard T. Mars

*Attorney, Agent, or Firm*—Sughrue, Mion, Zinn, Macpeak and Seas

[57]  ABSTRACT

A process for producing methyl tertiary butyl ether is disclosed, comprising reacting isobutylene and methanol using a hydrocarbon mixture of 4 carbon atoms containing isobutylene and methanol as starting materials in a reaction zone containing an acidic ion exchange resin and distilling the resulting reaction mixture in a distillation column connected to the reaction zone to separate methyl tertiary butyl ether from the unreacted hydrocarbon mixture of 4 carbon atoms, wherein a mixture of the hydrocarbon mixture of 4 carbon atoms as a distillate from a top of the distillation column and methanol as a distillate by azeotropy is contacted with water in a second extraction step to wash and extract methanol with water, and the water containing the extracted methanol is then contacted with said hdyrocarbon mixture of 4 carbon atoms containing isobutylene which is fed to the reaction zone in a first extraction step in an upstream of the reaction zone to thereby transfer a part or a large portion of the methanol in the methanol-containing water into a hydrocarbon mixture phase by reverse extraction. By the process, methanol in the reaction mixture can be recovered simply and at low cost.

8 Claims, 1 Drawing Figure

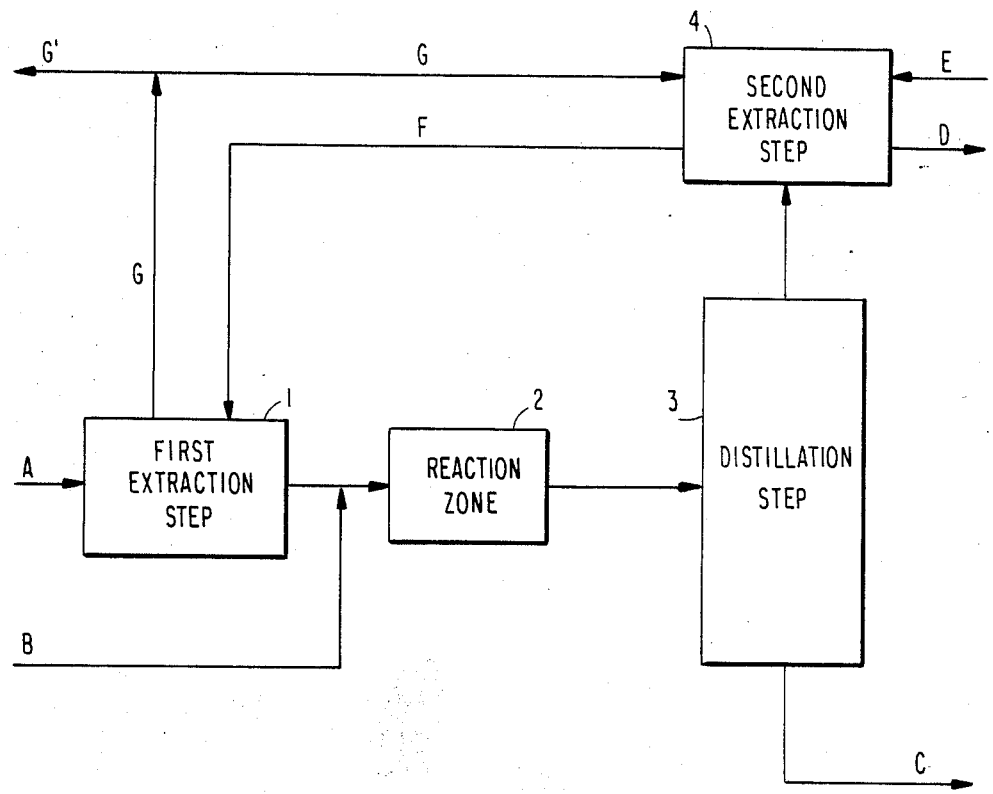

PROCESS FOR PRODUCING METHYL TERTIARY BUTYL ETHER

FIELD OF THE INVENTION

This invention relates to a process for producing methyl tertiary butyl ether (hereinafter referred to MTBE) that is useful as an additive for gasoline or a starting material for preparing isobutylene. More particularly, it relates to a process for producing MTBE by reacting isobutylene and methanol in the presence of an acidic ion exchange resin.

BACKGROUND OF THE INVENTION

It is widely known that MTBE can be prepared from isobutylene and methanol using an acidic ion exchange resin as a catalyst. An isobutylene source to be used therefor usually includes a hydrocarbon fraction having 4 carbon atoms ($C_4$ fraction) which is a by-product produced from an ethylene plant, a so-called spent B—B fraction that is a $C_4$ fraction from which 1,3-butadiene has been removed, a so-called FCC $C_4$ fraction that is a by-product produced from a catalytic cracking facility which is widely employed in recent years, and the like. These $C_4$ fractions will hereinafter be referred to "$C_4$ hydrocarbon mixture".

In the production of MTBE from the $C_4$ hydrocarbon mixture containing isobutylene and methanol in the presence of an acidic ion exchange resin, it is well known that a methanol feed exerts a great influence on an isobutylene recovery. In case when the methanol feed is less than a chemical equivalent for the reaction with isobutylene, by-production of dimers and trimers of isobutylene increases. Therefore, methanol is generally fed in excess, usually in an amount of from the chemical equivalent to twice the chemical equivalent to isobutylene to suppress formation of oligomers. However, feeding of excessive methanol results in an increase in cost for recovery of the excess. Even if the amount of methanol to be fed is less than the chemical equivalent amount, methanol unavoidably remains unreacted because the reaction between isobutylene and methanol is an equilibrium reaction. Thus, from the economical viewpoint, recovery of methanol is essential and has generally been conducted by washing extraction with water, distillation, and the like.

For example, U.S. Pat. No. 4,219,678 discloses a process for producing MTBE which comprises separating unreacted hydrocarbons from a reaction mixture, distilling the reaction mixture under pressure, and recovering pure MTBE from a bottom of a distillation column while recycling a methanol-containing distillate which is formed during the distillation to a reaction zone of methanol and isobutene. This process, however, has many problems. That is, since methanol is recovered taking advantage of azeotropy of methanol and MTBE, evaporation of the entrained MTBE requires a great deal of energy. Further, the distillation column should be operated under a high pressure in order to ensure higher recovery rate, which causes a significant increase of construction cost of facilities. Moreover, a heat source for high temperatures is required. In addition, in the separation of the unreacted hydrocarbons from MTBE, methanol is also separated as an azeotropic mixture with the unreacted hydrocarbons. Therefore, it is necessary to recover methanol from the distilled unreacted hydrocarbons by washing extraction with water and the like.

On the other hand, U.S. Pat. No. 4,544,776 discloses a process in which a reaction mixture immediately after withdrawal from a reaction zone is washed with water, and an extract containing methanol is distilled to separate methanol from water, said methanol being recycled to the reaction zone, while a raffinate left after the methanol removal is distilled to separate MTBE from unreacted hydrocarbons. This process, also, requires high energy since methanol is recovered by washing extraction with water, followed by distillation.

SUMMARY OF THE INVENTION

Accordingly, an object of this invention is to provide a process for producing MTBE from isobutylene and methanol, by which remaining methanol can be recovered more simply and at lower cost as compared with the conventional processes involving complicated steps and requiring high energy.

The present invention relates to a process for producing MTBE, which comprises reacting isobutylene and methanol using the $C_4$ hydrocarbon mixture containing isobutylene and methanol as starting materials in a reaction zone containing an acidic ion exchange resin and distilling the resulting reaction mixture in a distillation column connected to the reaction zone to separate MTBE from the unreacted $C_4$ hydrocarbon mixture, wherein a mixture of the $C_4$ hydrocarbon mixture as a distillate from a top of the distillation column and methanol as a distillate by azeotropy is contacted with water in a second extraction step to wash and extract methanol with water, and the water containing the extracted methanol is then contacted with said $C_4$ hydrocarbon mixture containing isobutylene which is fed to the reaction zone in a first extraction step installed in an upstream of the reaction zone, to thereby transfer a part or a large portion of the methanol in the methanol-containing water into a hydrocarbon mixture phase by reverse extraction and, if necessary, methanol is added to the hydrocarbon mixture phase and then fed to the reaction zone.

The above-described object of this invention can be accomplished by this process.

BRIEF DESCRIPTION OF THE ACCOMPANYING DRAWING

The FIGURE is a flow chart briefly illustrating the process of the invention. In the FIGURE, the numbers and alphabets indicate steps and streams as follows:
  1: First extraction step
  2: Reaction zone
  3: Distillation step
  4: Second extraction step
  A: $C_4$ Hydrocarbon mixture stream
  B: Methanol stream
  C: MTBE stream
  D: Unreacted $C_4$ hydrocarbon stream
  E: Water
  F: Extracted methanol-containing water stream
  G: Circulating water stream
  G': Waste water stream

DETAILED DESCRIPTION OF THE INVENTION

The $C_4$ hydrocarbon mixture which can be used in the process of the present invention includes the aforesaid $C_4$ fraction, spent B—B fraction, FCC $C_4$ fraction, etc. Examples of the acidic ion exchange resin which can be used in the present invention are Duolite C-26 (a trade name, produced by Diamond Shamrock Chemical), Amberlist 15 (a trade name, produced by Rohm & Haas Co.), etc.

A suitable amount of methanol to be fed ranges from about 0.9 to 1.6 moles and preferably from about 0.95 to 1.3 moles, per mole of isobutylene in the $C_4$ hydrocarbon mixture. Too a low feed of methanol causes by-production of dimers and trimers of isobutylene, etc. Excess methanol finally results in an increased concentration proportion of methanol in MTBE and is, therefore, unfavorable from the standpoint of product purity. A most preferred amount of methanol to be fed is such that almost all of the unreacted methanol can be distilled as an azeotropic mixture with the $C_4$ hydrocarbon mixture in the distillation column connected to the reaction zone, but such a distillate composition depends on the operating pressure and temperature of distillation, etc.

The mixture of the unreacted hydrocarbon and methanol which is separated from MTBE by distillation is then washed with water in the second extraction step at a temperature of from about 20° C. to 70° C. and preferably from about 30° C. to 60° C. under such a pressure that the contents in the extraction step can be maintained as a liquid state. The proportion of the unreacted hydrocarbon to water to be fed is from about 30:1 to 3:1 and preferably from about 20:1 to 7:1, by weight. The extracted methanol-containing water is then fed to the first extraction step in an upstream of the reaction zone where it is contacted with the isobutylene-containing $C_4$ hydrocarbon mixture to be fed to the reaction zone. It would be apparent from the proportion of hydrocarbon to water in the second extraction step that the proportion of the $C_4$ hydrocarbon mixture to the extracted methanol-containing water in the first extraction step is naturally determined by the conversion rate of isobutylene in the reaction zone, i.e., the production rate of the unreacted hydrocarbon, with respect to the proportion of the $C_4$ hydrocarbon mixture to the water exclusive of methanol.

The first extraction step can be carried out at a temperature ranging from about 20° C. to 70° C. and preferably from about 30° C. to 60° C. under such a pressure that the contents in the extraction step can be maintained as a liquid state.

It is possible to reuse a waste water withdrawn from the first extraction step by recycling to the second extraction step.

This invention will now be illustrated in greater detail with reference to the following examples, but it should be understood that they are not intended to limit the present invention.

EXAMPLE 1

Into a reaction vessel packed with 15 liters of an acidic ion exchange resin, Duolite C-26, were introduced 10 kg/hr of a $C_4$ hydrocarbon mixture having a composition as shown in Table 1 below and 2.1 kg/hr of methanol at a temperature of 50° C. under a pressure of 20 kg/cm$^2$G. By the reaction, isobutylene was selectively converted to MTBE at a conversion of 96%. The reaction mixture withdrawn from the reaction vessel had a composition shown in Table 2 below.

TABLE 1

| Composition of Starting Material | Proportion (wt %) |
|---|---|
| Isobutylene | 37.0 |
| 1-Butene | 10.3 |
| 2-Butene | 8.2 |
| n-Butane | 20.5 |
| Isobutane | 23.0 |
| 1,3-Butadiene | 0.5 |
| Others | balance |

TABLE 2

| Composition of Reaction Mixture | Proportion (wt %) |
|---|---|
| $C_4$—Hydrocarbon | 53.2 |
| MTBE | 45.1 |
| Methanol | 0.85 |
| Dimethyl ether | 0.1 |
| Diisobutylene | 0.45 |
| t-Butyl alcohol | 0.14 |
| Others | balance |

The reaction mixture was then distilled in a distillation column having 24 theoretical plates under a pressure of 4.5 kg/cm$^2$G, at a column top temperature of 48° C., and at a reflux ratio of 0.5 to obtain 5.6 kg/hr of MTBE containing 0.3 wt% of methanol from the bottom and 6.5 kg/hr of an unreacted $C_4$ hydrocarbon fraction containing 1.3 wt% of methanol and 0.2 wt% of dimethyl ether. The column top distillate in a dispersed phase was then contacted with 0.6 kg/hr of water in a perforated plate extraction column having 4 theoretical plates at a temperature of 40° C. under a pressure of 8 kg/cm$^2$G to obtain 0.68 kg/hr of methanol-water mixture containing 0.08 kg/hr of methanol. Thus separated $C_4$ hydrocarbon fraction contained about 0.1 wt% of methanol. The methanol-water mixture (0.68 kg/hr) was contacted with 10 kg/hr of a $C_4$ hydrocarbon mixture having the composition as shown in Table 1 which was to be fed to the MTBE synthesis reaction zone in a perforated plate extraction column having 10 theoretical plates at a temperature of 40° C. under a pressure of 8 kg/cm$^2$G, whereby 64 g/hr of methanol was transferred into the $C_4$ hydrocarbon mixture. The methanol content in the waste water was 2.6 wt%. Thus, about 80% of the methanol was recovered.

EXAMPLE 2

The reaction and distillation were carried out under the same conditions as described in Example 1 to obtain a column top distillate having the same composition as in Example 1. The column top distillate was contacted with 2 kg/hr of water in a perforated plate extraction column having 4 theoretical plates at a temperature of 40° C. under a pressure of 8 kg/cm$^2$G to obtain 2.084 kg/cm$^2$ of methanol-water mixture containing 0.084 kg/hr of methanol that was almost the whole quantity of methanol present in the distillate. Any residual methanol in the raffinate, i.e., $C_4$ fraction, was not detected. The methanol-water mixture (2.084 kg/hr) was then contacted with a $C_4$ hydrocarbon mixture having the composition as shown in Table 1 that was to be fed to the MTBE synthesis reaction zone in a perforated plate extraction column having 10 theoretical plates, whereby 0.024 kg/hr of methanol was transferred into the $C_4$ hydrocarbon, with the methanol concentration in the waste water being 2.9 wt%. Thus, about 30% of the methanol was recovered.

EXAMPLE 3

Into a reaction vessel packed with 15 liters of an acidic ion exchange resin (Duolite C-26) were introduced 10 kg/hr of a $C_4$ hydrocarbon mixture having a composition shown in Table 3 and 2.92 kg/hr of methanol at a temperature of 50° C. under a pressure of 20 kg/cm$^2$G. By the reaction, isobutylene was selectively converted to MTBE at a conversion of 95%. The reaction mixture withdrawn from the reaction vessel had a composition as shown in Table 4.

TABLE 3

| Composition of Starting Material | Proportion (wt %) |
| --- | --- |
| Isobutylene | 51.2 |
| 1-Butene | 22.2 |
| 2-Butene | 15.4 |
| n-Butane | 8.2 |
| Isobutane | 2.2 |
| 1,3-Butadiene | 0.7 |
| Others | balance |

TABLE 4

| Composition of Reaction Mixture | Proportion (wt %) |
| --- | --- |
| $C_4$—Hydrocarbon | 39.8 |
| MTBE | 57.9 |
| Methanol | 1.28 |
| Dimethyl ether | 0.2 |
| Diisobutylene | 0.59 |
| t-Butyl alcohol | 0.15 |
| Others | balance |

The resulting reaction mixture was distilled in a distillation column having 24 theoretical plates under a pressure of 4.5 kg/cm$^2$G, at a column top temperature of 49° C., and at a reflux ratio of 0.7 to obtain 7.6 kg/hr of MTBE containing 0.13 wt% of methanol from the bottom and 5.32 kg/hr of an unreacted $C_4$ hydrocarbon fraction containing 2.9 wt% of methanol and 0.49 wt% of dimethyl ether as a column top distillate. The column top distillate in a dispersed phase was contacted with 0.6 kg/hr of water in a perforated plate extraction column having 4 theoretical plates at a temperature of 40° C. under a pressure of 8 kg/cm$^2$G to obtain 0.74 kg/hr of methanol-water mixture containing 0.14 kg/hr of methanol. The residual methanol content in the unreacted $C_4$ hydrocarbon fraction was about 0.27 wt%. The methanol-water mixture (0.74 kg/hr) was then contacted with 10 kg/hr of a $C_4$ hydrocarbon mixture having the composition as shown in Table 3 which was to be fed to the MTBE synthesis reaction zone in a perforated plate extraction column having 10 theoretical plates at a temperature of 40° C. under a pressure of 8 kg/cm$^2$G, whereby 0.12 kg/hr of methanol was transferred into the $C_4$ hydrocarbon mixture, with the methanol content in the waste water being 3.2 wt%. Thus, about 86% of the methanol was recovered.

EXAMPLE 4

Into a reaction vessel packed with 15 liters of an acidic ion exchange resin (Duolite C-26) were introduced 10 kg/hr of a $C_4$ hydrocarbon mixture having a composition as shown in Table 5 and 0.86 kg/hr of methanol at a temperature of 50° C. under a pressure of 20 kg/cm$^2$G. By the reaction, isobutylene was selectively converted to MTBE at a conversion of 93%. The reaction mixture withdrawn from the reaction vessel had a composition as shown in Table 6.

TABLE 5

| Composition of Starting Material | Proportion (wt %) |
| --- | --- |
| Isobutylene | 15.0 |
| 1-Butene | 13.6 |
| 2-Butene | 13.8 |
| n-Butane | 7.5 |
| Isobutane | 49.6 |
| 1,3-Butadiene | 0.4 |
| Others | balance |

TABLE 6

| Composition of Reaction Mixture | Proportion (wt %) |
| --- | --- |
| $C_4$—Hydrocarbon | 79.2 |
| MTBE | 19.8 |
| Methanol | 0.59 |
| Dimethyl ether | 0.08 |
| Diisobutylene | 0.14 |
| t-Butyl alcohol | 0.16 |
| Others | balance |

The resulting reaction mixture was distilled in a distillation column having 24 theoretical plates under a pressure of 4.5 kg/cm$^2$G, at a column top temperature of 47° C., and at a reflux ratio of 0.34 to obtain 2.18 kg/hr of MTBE substantially free from methanol from the bottom of the column and 8.68 kg/hr of an unreacted $C_4$ hydrocarbon fraction containing 0.77% of methanol and 0.1% of dimethyl ether as a column top distillate. The column top distillate in a dispersed phase was then contacted with 0.6 kg/hr of water in a perforated plate extraction column having 4 theoretical plates at a temperature of 40° C. under a pressure of 8 kg/cm$^2$G to obtain 0.667 kg/hr of methanol-water mixture containing 67 g/hr of methanol. The residual methanol content in the unreacted $C_4$ hydrocarbon fraction was about 0.1 wt%. The methanol-water mixture (0.667 kg/hr) was contacted with 10 kg/hr of a $C_4$ hydrocarbon mixture having the composition as shown in Table 5 which was to be fed to the MTBE synthesis reaction zone in a perforated plate extraction column having 10 theoretical plates at a temperature of 40° C. under a pressure of 8 kg/cm$^2$G, whereby 55 g/hr of methanol was transferred into the $C_4$ hydrocarbon mixture, with the methanol content in the waste water being 2.0 wt%. Thus, about 82% of the methanol was recovered.

As demonstrated above, the present invention provides an efficient process for producing MTBE.

While the invention has been described in detail and with reference to specific embodiments thereof, it will be apparent to one skilled in the art that various changes and modifications can be made therein without departing from the spirit and scope thereof.

What is claimed is:

1. A process for producing methyl tertiary butyl ether comprising reacting isobutylene and methanol using a hydrocarbon mixture of 4 carbon atoms containing isobutylene and methanol as starting materials in a reaction zone containing an acidic ion exchange resin and distilling the resulting reaction mixture in a distillation column connected to the reaction zone to separate methyl tertiary butyl ether from the unreacted hydrocarbon mixture of 4 carbon atoms, wherein a mixture of the hydrocarbon mixture of 4 carbon atoms as a distillate from a top of the distillation column and methanol as a distillate by azeotropy is contacted with water in a second extraction step to wash and extract methanol with water, and the water containing the extracted methanol is then contacted with said hydrocarbon mixture of 4 carbon atoms containing isobutylene which is fed to the reaction zone in a first extraction step in an upstream of the reaction zone, to thereby transfer a part or a large portion of the methanol in the methanol-containing water into a hydrocarbon mixture phase by reverse extraction.

2. A process as in claim 1, wherein the first and second extraction steps are carried out at a temperature of from about 20° to 70° C. under such a pressure that the contents in the extraction step can be maintained as a liquid state.

3. A process as in claim 2, wherein the first and secone extraction steps are carried out at a temperature of from about 30° C. to 60° C.

4. A process as in claim 1, wherein the proportion of water to be fed to the second extraction step to the unreacted hydrocarbon is from about 1:3 to 1:30 by weight.

5. A process as in claim 4, wherein the proportion of water to be fed to the second extraction step to the unreacted hydrocarbon is from about 1:7 to 1:20 by weight.

6. A process as in claim 1, wherein methanol is fed to the reaction zone in an amount of from about 0.9 to 1.6 moles per mole of isobutylene in the hydrocarbon mixture of 4 carbon atoms.

7. A process as in claim 6, wherein methanol is fed to the reaction zone in an amount of from about 0.95 to 1.3 moles per mole of isobutylene in the hydrocarbon mixture of 4 carbon atoms.

8. A process as in claim 1, wherein the process further includes adding methanol to the hydrocarbon mixture phase to which methanol has been transferred.

* * * * *